United States Patent [19]

Tsang et al.

[11] 4,405,499

[45] Sep. 20, 1983

[54] ZEOLITE-RUTHENIUM-BORANE CATALYST COMPOSITION

[75] Inventors: Wen-Ghih Tsang, Framingham, Mass.; Lynn H. Slaugh, Cypress, Tex.

[73] Assignee: Shell Oil Company, Houston, Tex.

[21] Appl. No.: 410,298

[22] Filed: Aug. 23, 1982

[51] Int. Cl.³ ........................ B01J 29/12; B01J 21/02
[52] U.S. Cl. ................................ 252/432; 252/455 Z
[58] Field of Search ........................ 252/432, 455 Z; 423/118, 328

[56] References Cited

U.S. PATENT DOCUMENTS

| | | | |
|---|---|---|---|
| 2,952,721 | 9/1960 | Thomas et al. | 252/432 X |
| 3,200,083 | 8/1965 | Milton | 252/455 Z |
| 3,210,157 | 10/1965 | Lewis, Jr. et al. | 252/432 X |
| 3,647,717 | 3/1972 | Bolton | 252/455 Z |
| 3,954,670 | 5/1976 | Pine | 252/432 |
| 3,963,788 | 6/1976 | Kruse et al. | 252/455 Z |
| 4,115,424 | 9/1978 | Unland et al. | 252/432 |

*Primary Examiner*—Carl F. Dees

[57] ABSTRACT

A composition useful in catalytic reactions comprising ruthenium metal on a faujasite-type of zeolite which is subsequently treated with a borane solution under special conditions is disclosed here.

2 Claims, No Drawings

ZEOLITE-RUTHENIUM-BORANE CATALYST COMPOSITION

FIELD OF THE INVENTION

This invention relates to a catalyst composition comprising ruthenium metal on a zeolite support which is subsequently treated with borane. Such compositions are useful in syngas catalysis, hydrogenation reactions and dimerization processes.

BACKGROUND OF THE INVENTION

Supported ruthenium catalysts have been utilized in syngas reactions, hydrogenation reactions, and oligimerization reactions. The instant compositions comprising zeolite supported ruthenium treated with borane exhibit catalytic priorities significantly different from traditionally supported ruthenium compounds.

SUMMARY OF THE INVENTION

The instant invention comprises catalyst compositions prepared by ion exchanging ruthenium containing solutions with faujasite type zeolites, calcining and then reducing the ruthenium containing zeolite, subsequently contacting the ruthenium containing zeolite with borane, and subsequently calcining in nitrogen and reducing the borane treated material. Compositions prepared in this fashion have catalytic properties that differ from traditionally supported ruthenium materials such as for example ruthenium supported on zeolite alone, or ruthenium on a silica-alumina. They also differ significantly from similar compositions described in applicants' copending application Ser. NO. 410,299, filed Aug. 12, 1982 wherein the composition is calcined in air just prior to the final reduction.

DESCRIPTION OF THE PREFERRED EMBODIMENTS

The instant invention comprises a catalyst composition prepared by:

a. ion-exchanging the sodium ions of the sodium form of a faujasite type zeolite with ruthenium ions by contacting said zeolite with a solution containing a soluble ruthenium compound, b. calcining the ruthenium exchanged zeolite in nitrogen at a temperature ranging from about 300° C. to about 600° C.

c. contacting the ruthenium-containing zeolite with hydrogen at a temperature ranging from about 300° C. to about 600° C. whereby the ruthenium is reduced to the metal, d. contacting the ruthenium metal-containing zeolite with a solution of borane, e. calcining the borane-treated zeolite in nitrogen at a temperature ranging from about 300° C. to about 600° C. and then f. contacting the borane-treated zeolite with hydrogen at a temperature ranging from about 300° C. to about 600° C.

The zeolite used in the instant invention is of the faujasite type and is utilized initially in the sodium form, that is, the various exchange sites are satisfied by sodium. Such zeolites are described in U.S. Pat. Nos. 2,882,244, usually referred to as X zeolite and 3,216,789 referred to as a Y zeolite, and also in 3,446,727. These faujasitic type zeolites have been widely employed in catalytic processes such as for the conversion of hydrocarbons and are generally well known. The patent and general literature is extensive on these. In preparing the instant compositions, the sodium form of the faujasite type zeolite is contacted with a solution of a ruthenium salt whereby the ruthenium ion is ion-exchanged with the sodium ion. Any suitable, soluble ruthenium salt can be utilized, dissolved in an appropriate solvent. Suitable salts and solvents are readily determined by one skilled in the art. Illustrative examples of suitable ruthenium salts include salts such as ruthenium (III) chloride hydrate, ruthenium (III) bromide, anhydrous ruthenium (III) chloride and ruthenium nitrate. Also suitable are the ammonia complexes of the ruthenium halide such as for example $Ru(NH_3)_6Cl_3$ and $Ru(NH_3)_6I_3$. Salts of suitable organic acids are also suitable. Here, examples include ruthenium (III) acetate, ruthenium (III) propionate, ruthenium hexafluoracetylacetonate, ruthenium (III) triofluoracetate, ruthenium octanoate, ruthenium naphthenate, ruthenium valerate, and ruthenium (III) acetylacetoneate.

Suitable solvents for the desired ruthenium compounds can readily be determined by simple experimentation. Preferred solvents are water and the lower alkanols. After contacting the sodium form of the zeolite with the ruthenium-containing solution, the ruthenium-exchanged zeolite is dried and then calcined in nitrogen at a temperature ranging from about 300° C. to about 600° C. Calcination times are not critical and range from about 0.1 to about 20 hours. After calcination, the ruthenium-containing zeolite is reduced in a hydrogen atmosphere at a temperature ranging from about 300° C. to about 600° C. The reaction time is not critical but is adjusted according to the temperature of reduction, higher reduction temperatures will require shorter times and vice versa. Generally, times range from about 0.1 to about 20 hours. The reduction conditions are chosen such as to reduce the ruthenium which is an ionic form in the zeolite to ruthenium metal which will be deposited on the surfaces (external and pore volume) of the zeolite.

The ruthenium metal containing zeolite is then contacted with a solution of borane ($BH_3$ or diborane $B_2H_6$) in a suitable organic solvent. Suitable solvents comprises the ether solvents, particularly suitable is tetrahydrofuran,. The borane is typically prepared by the reaction of a metal hydride with a boron halide in an ether-type solvent. The borane compounds are sensitive to both air and moisture so the above mentioned impregnation of the zeolite with the borane compound must be maintained under anhydrous, air-free conditions.

After the zeolite has been impregnated with the borane solution, it is dried at relatively low temperatures up to about 50° C., and then calcined in nitrogen at a temperature ranging from about 300° C. to about 600° C. The calcined borane-treated zeolite is then reduced in a hydrogen atmosphere at a temperature ranging from about 300° C. to about 600° C. Calcination and reduction times are not critical and range from about 0.1 to about 20 hours.

The resultant catalytic material is used in a fashion typical of that utilized for heterogenous catalysts. It may be used in fixed beds, in fluidized beds or in batch reactors. The preparation of the catalytic compositions and their use in typical processes will be further described below by the following illustrative embodiments which are provided for illustration and are not to be construed as limiting the invention.

ILLUSTRATIVE EMBODIMENTS

Composition Preparation

The following example illustrates the typical preparation of a composition falling within the scope of the instant invention. 30 Grams of $Ru(NH_3)_6Cl_3$ are dissolved in 150 cc of water and added to a 50 cc condensing flask. 60 Milliliters of the sodium form of Y zeolite (L24-52/RW Linde) was calcined for 24 hours at 500° C. and then added to the reflux flask and refluxed for about two hours. The zeolite was the filtered and washed with approximately 500 cc of water. The zeolite was then placed in a quartz flow tube and calcined in a nitrogen flow (at about 550° C. for about five hours). The temperature was raised from room temperature to 550° C. at a rate of approximately 10° C. per minute. After calcining, the quartz flow tube was cooled and the hydrogen flow was initiated through the tube. The temperature was then again raised to about 500° C. at a rate of about 10° C. per minute. The material was maintained at 500° C. for about two hours. After reduction the sample was cooled to room temperature. Twenty-five cubic centimeters of the ruthenium-treated zeolite was contacted with 125 cc of a one molar solution of $BH_3$ in tetrahydrofuran. The borane-treated material was then dried at about 40° C. on a rotovac dryer for about three hours. The sample was then placed in a quartz tube, nitrogen flow was initiated and the tube was heated at about 10° C. per minute to about 550° C. for about five hours. After calcination the sample was cooled, hydrogen flow was then initiated over the sample, and the sample was heated to about 500° C. at a rate of about 10°0 C. per minute for about two hours. After this reduction, the sample was cooled overnight. During the above preparative techniques, the sample was maintained under dry box conditions except for the calcination and reduction process.

PROCESS

Syngas Reaction

The composition, according to this invention, (Example 1) was prepared in the fashion described above. Analysis of this composition showed that it had approximately 6 wt. % ruthenium and about 0.97 wt. % boron. The sample was placed in a tubular flow reactor and heated to the appropriate reaction temperature as indicated in Table 1. Carbon monoxide and hydrogen in a molar ratio of about 1:1 were fed to the reactor under the conditions indicated in Table 1. The products of the reactor were analyzed by gas chromotography and the results are shown in Table 1 below. For comparative purposes, other compositions not falling within the scope of this invention were prepared. Example A comprises a ruthenium metal supported on a Y zeolite. This is basically the same as Example 1 without the borane treatment. Example B comprises the use of an alumina-silica as a support rather than a zeolite. The aluminasilica is Davison 980-25 which has a similar Al/Si ratio as the Y zeolite. This example was prepared in the same fashion as Example 1. Example C is substantially the same as Example B without the borane treatment. Example D comprises a composition prepared according to the teachings of applicants' copending application Ser. No. 410,299, filed Aug. 23, 1982 wherein just prior to the final reduction the composition is calcined in air rather than nitrogen. As can be seen from the table, the composition of the instant invention provides a much higher yield of oxygenates (alcohols and aldehydes) than the other comparative examples.

1. Hexene Oligomerization

A composition similar to that of Example 1 above was placed in a flow reactor and heated to reaction temperature. 1-Hexene was passed over the reactor. Analysis of the products showed the presence of $C_{12}$ and $C_{18}$ oligomers.

TABLE 1

Syngas Conversions by Ru/B/Y and Related Catalysts

| Catalyst: | | 1<br>Ru/B/Y | A<br>Ru/Y | B<br>Ru/B/Al—Si* | C<br>Ru/Al—Si* | D<br>Ru/B/Y |
|---|---|---|---|---|---|---|
| Ru % | | 6.00 | 7.10 | 3.96 | 3.96 | 7.1 |
| B % | | 0.97 | — | 0.75 | — | 1.02 |
| GHSV | | 4000 | 4000 | 3000 | 4000 | 4300 |
| Temperature (°C.) | | 250 | 220 | 250 | 250 | 250 |
| Pressure (PSIG) | | 1500 | 1800 | 1000 | 1500 | 1000–1500 |
| % Syngas (1:1) Conversion | | 6.4 | 5.1 | 11.5 | 2.8 | 15.5 |
| Molar Selectivity % | | | | | | |
| $C_1$ | Methane | 20.6 | 12.8 | 8.9 | 22.6 | 3.2 |
| | Methanol | 3.8 | 0.6 | — | 0.78 | 0.4 |
| $C_2$ | Ethylene/Ethane | 2.4/— | 4.0/0.6 | 2.4/0.6 | 7.1/— | 1.5/— |
| | Ethanol | 1.8 | — | — | — | — |
| $C_3$ | Propene/Propane | 0.3/2.4 | 1.1/2.2 | —/0.4 | —/4.1 | —/— |
| | Propanol | — | — | — | — | — |
| $C_4$ | Butene/Butane | 2.0/8.8 | —/11.7 | 3.5/7.7 | 3.4/14.2 | —/2.9 |
| | Butanol | — | — | — | — | — |
| $C_5^+$ | | 57.9 | 67.2 | 76.3 | 46.9 | 91.0 |
| In $C_5^+$ | Paraffins | 41.4 | 54.7 | 57.8 | 50.7 | |
| | Olefins | 16.4 | 31.0 | 34.2 | 31.2 | |
| | Alcohols | 24.6 | 5.5 | 1.4 | 10.6 | |
| | Aldehydes | 11.9 | 3.2 | 2.3 | 6.7 | $C^{30}$ |
| Overall | Paraffins | 57.5 | 64.0 | 64.2 | 64.6 | Paraffins |
| | Olefins | 14.2 | 25.7 | 31.9 | 25.1 | |
| | Alcohols | 19.8 | 4.4 | 1.1 | 5.8 | |
| | Aldehydes | 6.9 | 2.2 | 1.8 | 3.1 | |

*Davison 980-25 alumina-silicate which has similar Al/Si ratio as Y zeolite.

We claim:

1. A catalyst composition prepared by a process which comprises:
   a. ion-exchanging the sodium ions of the sodium form of a faujasite type zeolite with ruthenium ions by contacting said zeolite with a solution containing a soluble ruthenium compound,
   b. calcining the ruthenium exchange zeolite in nitrogen at a temperature ranging from about 300° C. to about 600° C.
   c. contacting the ruthenium-containing zeolite with hydrogen at a temperature ranging from about 300° C. to about 600° C. whereby the ruthenium is reduced to the metal,
   d. contacting the ruthenium metal-containing zeolite with a solution of borane,
   e. calcining the borane treated zeolite in nitrogen at a temperature ranging from about 300° C. to about 400° C. and then
   f. contacting the borane-treated zeolite with hydrogen at a temperature ranging from about 300° C. to about 400° C.

2. The composition of claim 1 where in the process an aqueous solution of $Ru(NH_3)_6 Cl_3$ is used in step a and a tetrahydrofuran solution of borane is used in step d.